United States Patent
Hunt et al.

(10) Patent No.: US 8,431,578 B2
(45) Date of Patent: Apr. 30, 2013

(54) ORGANIC COMPOUNDS

(75) Inventors: Peter Hunt, Storrington (GB);
Catherine Leblanc, Horsham (GB);
Robert Alexander Pulz, Basel (CH);
Nikolaus Johannes Stiefl, Lörrach (DE)

(73) Assignee: Novartis AG, Basel (CH)

( * ) Notice: Subject to any disclaimer, the term of this patent is extended or adjusted under 35 U.S.C. 154(b) by 323 days.

(21) Appl. No.: 12/810,948

(22) PCT Filed: Jan. 9, 2009

(86) PCT No.: PCT/EP2009/050222
§ 371 (c)(1),
(2), (4) Date: Aug. 12, 2010

(87) PCT Pub. No.: WO2009/087224
PCT Pub. Date: Jul. 16, 2009

(65) Prior Publication Data
US 2010/0298337 A1 Nov. 25, 2010

(30) Foreign Application Priority Data

Jan. 11, 2008 (EP) .................................. 08150194
Jun. 10, 2008 (EP) .................................. 08157985

(51) Int. Cl.
*A61K 31/497* (2006.01)
*A61K 31/513* (2006.01)
*A61K 31/506* (2006.01)
*C07D 401/14* (2006.01)

(52) U.S. Cl.
USPC ...... 514/252.18; 514/256; 514/269; 544/295; 544/319; 544/333

(58) Field of Classification Search ............. 514/252.18, 514/269, 256; 544/295, 319, 333
See application file for complete search history.

(56) References Cited

FOREIGN PATENT DOCUMENTS

| EP | 431 421 A2 | 6/1991 |
| WO | WO 03/027100 A1 | 4/2003 |
| WO | WO2004/013135 | 2/2004 |
| WO | WO2005/099711 A1 | 10/2005 |
| WO | WO2005/105303 A1 | 11/2005 |
| WO | WO2005/026306 | 3/2006 |
| WO | WO2007/110337 | 10/2007 |
| WO | WO2008/006583 | 1/2008 |
| WO | WO 2008/119689 | 10/2008 |

OTHER PUBLICATIONS

Vippagunta et al., Crystalline solids, 2001, Advanced Drug Delivery Reviews, 48, pp. 3 and 18.*
Database Beilstein and De Coma XP002482684, 1991.
Database Beilstein and Borowski XP002482685, 2000.
Database Beilstein and Makrosz XP002462686, 1994.
Database Beilstein XP002482687, 1964.
Database Beilstein and Twomey XP002462688, 1954.
Database Beilstein XP002485689 and Strekowski *Bull. Acad. Pol. Sci. Ser Sci. Chem.*, 1976.
Database Beilstein XP002462690 and Strekowski *Pol. J. Chem.*, 1978.
Database Beilstein XP002462601 and Kabbe *Justus Liebigs Ann. Chem.*, 1987.
Database Beilstein XP002482682 and Lafferty Case *J. Org. Chem.*, 1967.
Database Beilstein XP002482683 and Potts et al., *J. Org. Chem.*, 1983.
Database Beilstein XP002482094 and Kranmier, Frisky, 2000.
Database Beilstein XP002482695 and Boully et al., *J. Heterocycl. Chem.*, 2005.
Database Beilstein XP002525036, 1948.
Database Beilstein XP002525037, 1963.

* cited by examiner

*Primary Examiner* — Kristin Bianchi
(74) *Attorney, Agent, or Firm* — John B. Alexander

(57) ABSTRACT

Compounds of formula (I) in free or salt or solvate form, where $T^1$, $T^2$, and $T^3$ have the meanings as indicated in the specification, are useful for treating inflammatory or obstructive airways, pulmonary hypertension, pulmonary fibrosis, liver fibrosis, muscle diseases and systemic skeletal disorders. Pharmaceutical compositions that contain the compounds and processes for preparing the compounds are also described.

(I)

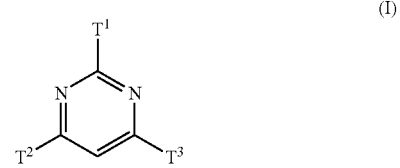

3 Claims, No Drawings

ORGANIC COMPOUNDS

This invention relates to organic compounds and their use as pharmaceuticals, in particular for the treatment of inflammatory or obstructive airways diseases, pulmonary hypertension, pulmonary fibrosis, liver fibrosis, cancer, muscle diseases such as muscle atrophies and muscle dystrophies, and systemic skeletal disorders such as osteoporosis.

In one aspect, the present invention provides a compound of formula I

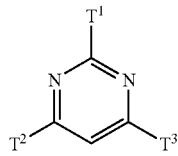

in free or pharmaceutically acceptable salt or solvate form, where $T^1$ is a 4- to 14-membered heterocyclic group containing one to three N-heteroatoms or $C_4$-$C_{15}$-cycloalkenyl, each optionally substituted at one, two or three positions by $R^1$, $C_1$-$C_8$-alkoxy, $C_3$-$C_5$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T^2$ is a 4- to 14-membered heterocyclic group optionally substituted at one, two or three positions by $R^1$, $R^2$, $R^5$, $C_1$-$C_8$-alkoxy, $C_1$-$C_8$-alkoxycarbonyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T^3$ is —H, —OH, halogen, $C_1$-$C_8$-alkyl, —C(O)$R^x$, —CH$_2$O$R^y$, —O$R^z$, —S$R^p$, CH(OH)$R^1$, C(OH)$R^1R^{1a}$ or CH(NHR$^8$)$R^1$, wherein the alkyl group is optionally substituted by one or more substituents selected from hydroxy, cyano, halo, $R^5$, —C(=O)—$R^5$, amino, $C_1$-$C_8$-alkylamino, di($C_1$-$C_8$-alkyl)amino, $C_1$-$C_8$-alkanoylamino, $C_1$-$C_8$-alkoxy, —C(=O)NR$^6$R$^7$, —NH(C=O)—$C_1$-$C_8$-alkyl and —SO$_2$NR$^6$R$^7$;

$R^1$ and $R^{1a}$ are each independently selected from $C_1$-$C_8$-alkyl, $C_2$-$C_8$-alkenyl, $C_3$-$C_8$-cycloalkyl and $C_2$-$C_8$-alkynyl, each optionally substituted at one, two or three positions by hydroxy, cyano, amino, halo, $R^5$, —C(=O)—$R^5$, $C_1$-$C_8$-alkylamino, di($C_1$-$C_8$-alkyl)amino, $C_1$-$C_8$-alkanoylamino, $C_1$-$C_8$-alkoxy, —C(=O)NR$^6$R$^7$, —NH(C=O)—$C_1$-$C_8$-alkyl or —SO$_2$NR$^6$R$^7$;

$R^2$ is $C_6$-$C_{15}$-aryl or $C_4$-$C_{15}$-cycloalkenyl, each optionally substituted at one, two or three positions by halo, hydroxy, $R^1$, $R^5$, $C_1$-$C_8$-alkylthio, cyano, COOH, CHO, nitro, —O—$C_6$-$C_{15}$-aryl, halo-$C_1$-$C_8$-alkyl, —NR$^6$R$^7$, —$C_1$-$C_8$-alkyl-NR$^6$R$^7$, —O—$C_1$-$C_8$-alkyl-NR$^6$R$^7$, —$C_1$-$C_8$-alkyl-$R^5$, —O—$R^1$ optionally substituted by NR$^6$R$^7$, —O—$R^5$, —C(=O)—$R^5$, —C(=O)—NH$_2$, —C(=O)NR$^6$R$^7$, —C(=O)—O—$R^1$, —O—C(=O)—$R^1$, —SO$_2$—NH$_2$, —SO$_2$—$R^1$, —NH—SO$_2$—$C_1$-$C_8$-alkyl, —C(=O)—NH—$R^1$, —C(=O)—NH—$R^5$, —SO$_2$—$C_6$-$C_{15}$-aryl, —SO$_2$—$R^5$ or —SO$_2$NR$^6$R$^7$;

$R^5$ is a 4- to 14-membered heterocyclic group optionally substituted at one, two or three positions by oxo, amino, halo, $C_1$-$C_8$-alkylamino, di($C_1$-$C_8$-alkyl)amino, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—NH$_2$ or —SO$_2$—NH$_2$;

$R^6$ and $R^7$ are independently hydrogen, —$R^1$, $C_6$-$C_{15}$-aryl, —$C_1$-$C_8$-alkyl-$C_6$-$C_{15}$-aryl, —$R^5$ or —$C_1$-$C_8$-alkyl-$R^5$;

$R^8$ is H or $R^1$;

$R^p$, $R^x$ and $R^y$ are independently $C_1$-$C_8$-alkyl, $C_2$-$C_8$-alkenyl, $C_3$-$C_8$-cycloalkyl or $C_2$-$C_8$-alkynyl, each optionally substituted at one, two or three positions by hydroxy, cyano, amino or halo;

$R^z$ is $C_1$-$C_8$-alkyl, $C_1$-$C_8$-alkyl-$C_6$-$C_{15}$-aryl, $C_1$-$C_8$-alkyl-Het, wherein the alkyl and aryl groups are each optionally substituted by at least one substituent selected from oxo, amino, halo, $C_1$-$C_8$-alkylamino, di($C_1$-$C_8$-alkyl)amino, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—NH$_2$ or —SO$_2$—NH$_2$, and Het is a 4- to 14-membered heterocyclic group optionally substituted at one, two or three positions by oxo, amino, halo, $C_1$-$C_8$-alkylamino, di($C_1$-$C_8$-alkyl)amino, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—NH$_2$ or —SO$_2$—NH$_2$.

Terms used in the specification have the following meanings:

"Optionally substituted at one, two or three positions" as used herein means the group referred to can be substituted at one or two or three positions by any one or any combination of the radicals listed thereafter. Thus, where two or more substituents are present, these may be the same or different.

"Halo" or "halogen" as used herein denotes a element belonging to group 17 (formerly group VII) of the Periodic Table of Elements, which may be, for example, fluorine, chlorine, bromine or iodine.

"$C_1$-$C_8$-alkyl" as used herein denotes straight chain or branched alkyl that contains one to eight carbon atoms. Where different numbers of carbon atoms are specified, such as $C_6$ or $C_4$, the definition should be construed accordingly.

"$C_2$-$C_8$-alkenyl" as used herein denotes straight chain or branched hydrocarbon chains that contain two to eight carbon atoms and one or more carbon-carbon double bonds. Where different numbers of carbon atoms are specified, such as $C_6$ or $C_4$, the definition should be construed accordingly.

"$C_2$-$C_8$-alkynyl" as used herein denotes straight chain or branched hydrocarbon chains that contain two to eight carbon atoms and one or more carbon-carbon triple bonds. Where different numbers of carbon atoms are specified, such as $C_6$ or $C_4$, the definition should be construed accordingly.

"$C_6$-$C_{15}$-aryl" as used herein denotes an aromatic group having 6- to 15-ring carbon atoms. Examples of $C_6$-$C_{15}$-aryl groups include but are not limited to phenyl, phenylene, benzenetriyl, indanyl, naphthyl, naphthylene, naphthalenetriyl and anthrylene.

"4- to 14-membered heterocyclic group" as used herein denotes a 4- to 14-membered heterocyclic ring containing at least one ring heteroatom selected from the group consisting of nitrogen, oxygen and sulphur, which may be saturated, partially saturated or unsaturated. Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydro-furan, tetrahydrothiophene, tetrahydrothiopyran, tetrahydropyran, 1,4-dioxane, 1,4-oxathiane, indazole, quinoline, indole, thiazole, isoquinoline, benzothiophene, benzoxazole, benzisoxazole, benzothiazole, benzoisothiazole, benzofuran, dihydrobenzofuran, benzodioxole, benzimidazole, tetrahydronaphthyridine, pyrrolopyridine, tetrahydrocarbazole, benzotriazole and tetrahydrothiopyranoindole. The 4- to 14-membered heterocyclic group can be unsubstituted or substituted.

"N-heterocyclic group" as used herein denotes a heterocyclic group wherein at least one of the ring atoms is a nitrogen atom. The N-heterocyclic group can be unsubstituted or substituted.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl, cyclohexyl, cycloheptyl, cyclooctyl, cyclononyl or cyclodecyl, or a bicyclic group such as bicycloheptyl or bicyclooctyl. Where different numbers of carbon atoms are specified, such as $C_6$, the definition should be construed accordingly.

"$C_4$-$C_{15}$-Cycloalkenyl" is a partially unsaturated carbocyclic, mono-, bi- or tricyclic ring with at least one double bond, such as cyclobutenyl, cyclopentenyl, e.g. cyclopenten-2- or -3-yl, cyclohexenyl, e.g. cyclohexen-2- or -3-yl, cycloheptenyl, e.g. cyclohepten-2-, -3- or -4-yl, cyclooctenyl, cyclononenyl or cyclodecenyl, or a bicyclic group such as bicycloheptenyl or bicyclooctenyl, and can be unsubstituted or substituted.

"Halo-$C_1$-$C_8$-alkyl" as used herein denotes $C_1$-$C_8$-alkyl as hereinbefore defined substituted by one or more halogen atoms, preferably one, two or three halogen atoms.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different.

"$C_1$-$C_8$-alkylthio" as used herein denotes straight chain or branched alkylthio having 1 to 8 carbon atoms. Where different numbers of carbon atoms are specified, such as $C_6$ or $C_4$, the definition should be construed accordingly.

"$C_1$-$C_8$-alkoxy" as used herein denotes straight chain or branched alkoxy that contains 1 to 8 carbon atoms. Where different numbers of carbon atoms are specified, such as $C_6$ or $C_4$, the definition should be construed accordingly.

"$C_1$-$C_8$-alkoxycarbonyl" as used herein denotes $C_1$-$C_8$-alkoxy as hereinbefore defined attached through the oxygen atom to a carbonyl group.

Where variables are defined with reference to other variables, e.g. $R^2$ is $C_6$-$C_{15}$ aryl optionally substituted by $R^1$ or $R^5$, this means that the $R^2$ group is optionally substituted by one or more substituents each independently selected from the definition of $R^1$ and/or $R^5$. Where a compound includes more than one substituent selected from the definition of a particular variable (e.g. $R^1$), each substituent may be the same or different.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

Suitable compounds of formula I include compounds in free or salt or solvate form wherein:

$T^1$ is a 5- to 7-membered heterocyclic group containing one or two N-heteroatoms, optionally substituted at one, or two positions by $R^1$, $C_1$-$C_4$-alkoxy, $C_3$-$C_5$-cycloalkyl, halo, hydroxy or nitro;

$T^2$ is a 5- to 7-membered N-heterocyclic group containing one or two N-heteroatoms, optionally substituted at one or two positions by $R^1$, $R^2$, $R^5$, $C_1$-$C_8$-alkoxy, $C_1$-$C_8$-alkoxycarbonyl or cyano;

$T^3$ is —H; —OH; halogen; $C_1$-$C_8$-alkyl optionally substituted by hydroxy, halo or amino; or —$OR^z$, $R^1$ is $C_1$-$C_4$-alkyl;

$R^2$ is $C_6$-$C_{10}$-aryl optionally substituted at one or two positions by halo, COOH, CHO, $R^1$, O—$R^1$, $R^5$, —$C_1$-$C_8$-alkyl-$R^5$, —C(=O)—$R^5$, —$SO_2$—$NH_2$, —$SO_2$—$R^1$, —NH—$SO_2$—$C_1$-$C_8$-alkyl, —C(=O)—NH—$R^1$, —C(=O)—NH—$R^5$ or by $C_1$-$C_8$-alkoxy optionally substituted at one position by di($C_1$-$C_8$-alkyl)amino;

$R^5$ is a 4- to 14-membered heterocyclic group optionally substituted at one, two or three positions by $C_1$-$C_8$-alkyl; and $R^z$ is $C_1$-$C_4$-alkyl, $C_1$-$C_4$-alkyl-$C_6$-$C_{10}$-aryl, $C_1$-$C_4$-alkyl-Het wherein Het is a 5- to 10-membered heterocyclic ring system, containing one or two N-heteroatoms, wherein the alkyl, aryl and Het groups are each optionally substituted by at least one substituent selected from oxo, amino, halo, $C_1$-$C_8$-alkylamino, di($C_1$-$C_8$-alkyl)amino, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—$NH_2$ or —$SO_2$—$NH_2$.

Further suitable compounds of formula I include compounds in free or salt or solvate form wherein:

$T^1$ is a 5- or 6-membered heterocyclic group containing one or two N-heteroatoms, optionally substituted at one position by $R^1$ or $C_1$-$C_4$-alkoxy;

$T^2$ is a 5- or 6-membered N-heterocyclic group optionally substituted at one or two positions by $R^1$, $R^2$, $R^5$, $C_1$-$C_4$-alkoxy, $C_1$-$C_4$-alkoxycarbonyl or cyano;

$T^3$ is —H; —OH; Cl; $C_1$-$C_6$-alkyl optionally substituted by halo, amino or hydroxy; or —$OR^z$;

$R^1$ is $C_1$-$C_4$-alkyl;

$R^2$ is phenyl optionally substituted at one or two positions by halo, COOH, CHO, $R^1$, O—$R^1$, $R^5$, —$C_1$-$C_8$-alkyl-$R^5$, —C(=O)—$R^5$, —$SO_2$—$NH_2$, —$SO_2$—$R^1$, —NH—$SO_2$—$C_1$-$C_8$-alkyl, —C(=O)—NH—$R^1$, —C(=O)—NH—$R^5$ or by $C_1$-$C_8$-alkoxy optionally substituted at one position by di($C_1$-$C_8$-alkyl)amino;

$R^5$ is a 4- to 14-membered heterocyclic group optionally substituted at one or two positions by $C_1$-$C_4$-alkyl; and $R^z$ is $C_1$-$C_3$-alkyl, $C_1$-$C_3$-alkyl-$C_6$-$C_{10}$-aryl, $C_1$-$C_3$-alkyl-Het wherein Het is a 6- to 9-membered heterocyclic ring system, containing one or two N-heteroatoms and wherein the alkyl, aryl and Het groups are each optionally substituted by at least one substituent selected from oxo, amino, halo, $C_1$-$C_8$-alkylamino, di($C_1$-$C_8$-alkyl)amino, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—$NH_2$ or —$SO_2$—$NH_2$.

According to formula I, the various embodiments of the invention may be incorporated independently, collectively or in any combination. Thus, a definition of a variable in one embodiment may be combined with a definition of a separate variable in a different embodiment described herein. Accordingly, the invention is intended to cover all combinations of embodiments or parts of embodiments and as such, the term "an embodiment of the invention" should be construed as "an embodiment or aspect of the invention as described or defined anywhere herein".

$T^1$ is suitably a 4- to 14-membered heterocyclic group containing one to three N-heteroatoms optionally substituted at one, two or three positions by $R^1$, $C_1$-$C_8$-alkoxy, $C_3$-$C_5$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro. Optionally, $T^1$ is a 6-membered N-heterocyclic group, containing one N heteroatom, optionally substituted at one position by $C_1$-$C_4$-alkyl (e.g. methyl, ethyl, iso-propyl, n-propyl, iso-butyl, n-butyl, t-butyl, but preferably methyl). For example $T^1$ may be unsubstituted pyridinyl, especially pyridin-2-yl, or pyridin-2-yl substituted by $C_1$-$C_4$-alkyl (especially methyl), for example 6-methyl-pyridin-2-yl.

$T^2$ is suitably a 6-membered N-heterocyclic group containing one N heteroatom, optionally substituted at one position by $C_1$-$C_4$-alkoxy or by $C_6$-$C_{15}$-aryl (especially phenyl) wherein said aryl group is optionally substituted by halo, $C_1$-$C_4$-alkoxy (especially methoxy), $R^5$, $C_1$-$C_4$-alkyl-$R^5$ or —C(=O)—$R^5$. For example $T^2$ is unsubstituted pyridinyl, especially unsubstituted pyridin-3-yl, or $T^2$ is pyridinyl, especially pyridin-3-yl, substituted by phenyl substituted at one position by $C_1$-$C_4$-alkoxy (e.g. methoxy, ethoxy, iso-propoxy, n-propoxy, iso-butoxy, n-butoxy, t-butoxy, but preferably methoxy), C(O)$R^5$ or $CH_2$—$R^5$. Preferred $T^2$ groups herein are selected from the group including unsubstituted pyridine-3-yl, and pyridine-3-yl groups substituted at the 5-position by 3-methoxyphenyl, phenyl substituted by (4-isopropyl-piperaziny-1-yl)methanone, or phenyl substituted by (4-isopropyl-piperaziny-1-yl)methyl.

$T^3$ is suitably H; Cl; OH; $C_1$-$C_6$-alkyl optionally substituted by OH, $NH_2$ or halo; or —Orz, wherein Rz is $C_1$-$C_3$-alkyl (especially methyl, or isopropyl), $C_1$-$C_2$-alkylphenyl, $C_1$-$C_2$-alkylHet. For example $T^3$ is H, Cl, OH, $^t$Bu, benzyloxy, -oxy-ethyl-1H-indole, methoxy, or isopropoxy;

$R^1$ is suitably $C_1$-$C_4$-alkyl optionally substituted at one position by hydroxy or halo.

$R^2$ is suitably $C_6$-$C_{15}$-aryl optionally substituted at one, two or three positions by halo, hydroxy, $R^1$, $R^5$, $C_1$-$C_8$-alkylthio, cyano, COOH, CHO, nitro, —O—$C_6$-$C_{15}$-aryl, halo-$C_1$-$C_8$-alkyl, —$NR^6R^7$, —$C_1$-$C_8$-alkyl-$NR^6R^7$, —O—$C_1$-$C_8$-alkyl-$NR^6R^7$, —$C_1$-$C_8$-alkyl-$R^5$, —O—$R^1$ optionally substituted by $NR^6R^7$, —O—$R^5$, —C(=O)—$R^5$, —C(=O)—$NH_2$, —C(=O)$NR^6R^7$, —C(=O)—O—$R^1$, —O—C(=O)—$R^1$, —$SO_2$—$NH_2$, —$SO_2$—$R^1$, —NH—$SO_2$—$C_1$-$C_8$-alkyl, —C(=O)—NH—$R^1$, —C(=O)—NH—$R^5$, —$SO_2$—$C_6$-$C_{15}$-aryl, —$SO_2$—$R^5$ or —$SO_2NR^6R^7$. Optionally, $R^2$ is $C_6$-$C_{10}$-aryl, especially phenyl, optionally substituted at one or two positions by halo, —$R^1$, —$C_1$-$C_4$-alkyl-$R^5$, —C(=O)—$R^5$, —$SO_2$—$NH_2$, —$SO_2$—$C_1$-$C_4$-alkyl, —NH—$SO_2$—$C_1$-$C_4$-alkyl, —C(=O)—NH—$R^5$ or $C_1$-$C_4$-alkoxy optionally substituted at one position by di($C_1$-$C_4$-alkyl)amino.

$R^5$ is suitably a 4- to 10-membered heterocyclic group (especially a 5- or 6-membered heterocyclic group) optionally substituted at one or two positions by oxo or $C_1$-$C_4$-alkyl. For example $R^5$ is piperazin-2-one, piperizinyl (especially piperizin-1-yl), morpholinyl, pyrazolyl, pyrrolidinyl, piperazinyl (especially piperazin-1-yl) or tetrahydropyranyl.

According to a further embodiment, the present invention relates to compounds of formula I, as Exemplified herein, independently selected from the group including:
4-Benzyloxy-6-[5-(3-methoxy-phenyl)-pyridin-3-yl]-2-pyridin-2-yl-pyrimidine,
(4-Isopropyl-piperazin-1-yl)-{4-[5-(2-pyridin-2-yl-pyrimidin-4-yl)-pyridin-3-yl]-phenyl}-methanone,
4-{5-[4-(4-Isopropyl-piperazin-1-ylmethyl)-phenyl]-pyridin-3-yl}-2-pyridin-2-yl-pyrimidine,
3-[2-(6-Pyridin-3-yl-2-pyridin-2-yl-pyrimidin-4-yloxy)-ethyl]-1H-indole,
3-{2-[2-(6-Methyl-pyridin-2-yl)-6-pyridin-3-yl-pyrimidin-4-yloxy]-ethyl}-1H-indole,
(4-{5-[6-Chloro-2-(6-methyl-pyridin-2-yl)-pyrimidin-4-yl]-pyridin-3-yl}-phenyl)-(4-isopropyl-piperazin-1-yl)-methanone,
(4-{5-[6-Benzyloxy-2-(6-methyl-pyridin-2-yl)-pyrimidin-4-yl]-pyridin-3-yl}-phenyl)-(4-isopropyl-piperazin-1-yl)-methanone,
(4-Isopropyl-piperazin-1-yl)-(4-{5-[6-methoxy-2-(6-methyl-pyridin-2-yl)-pyrimidin-4-yl]-pyridin-3-yl}-phenyl)-methanone,
(4-{5-[6-Hydroxy-2-(6-methyl-pyridin-2-yl)-pyrimidin-4-yl]-pyridin-3-yl}-phenyl)-(4-isopropyl-piperazin-1-yl)-methanone,
{4-[5-(6-Chloro-2-pyridin-2-yl-pyrimidin-4-yl)-pyridin-3-yl]-phenyl}-(4-isopropyl-piperazin-1-yl)-methanone,
{4-[5-(6-Benzyloxy-2-pyridin-2-yl-pyrimidin-4-yl)-pyridin-3-yl]-phenyl}-(4-isopropyl-piperazin-1-yl)-methanone,
{4-[5-(6-Isopropoxy-2-pyridin-2-yl-pyrimidin-4-yl)-pyridin-3-yl]-phenyl}-(4-isopropyl-piperazin-1-yl)-methanone,
4-tert-Butyl-6-{5-[4-(4-methyl-piperazin-1-ylmethyl)-phenyl]-pyridin-3-yl}-2-pyridin-2-yl-pyrimidine,
Dimethyl-((R)-1-{4-[5-(2-pyridin-2-yl-pyrimidin-4-yl)-pyridin-3-yl]-benzyl}-pyrrolidin-3-yl)-amine,
Dimethyl-((R)-1-{3-[5-(2-pyridin-2-yl-pyrimidin-4-yl)-pyridin-3-yl]-benzyl}-pyrrolidin-3-yl)-amine,
(4-{5-[6-Chloro-2-(6-methyl-pyridin-2-yl)-pyrimidin-4-yl]-pyridin-3-yl}-phenyl)-(3-dimethylamino-pyrrolidin-1-yl)-methanone,
(1-{4-[5-(6-Methoxy-2-pyridin-2-yl-pyrimidin-4-yl)-pyridin-3-yl]-benzyl}-pyrrolidin-3-yl)-dimethyl-amine,
(4-{5-[6-Benzyloxy-2-(6-methyl-pyridin-2-yl)-pyrimidin-4-yl]-pyridin-3-yl}-phenyl)-(3-dimethylamino-pyrrolidin-1-yl)-methanone,
4-tert-Butyl-6-{5-[4-(4-methyl-piperazin-1-ylmethyl)-phenyl]-pyridin-3-yl}-2-(6-methyl-pyridin-2-yl)-pyrimidine,
and free or salt or solvate forms thereof.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl groups, are also capable of forming salts with bases, in particular pharmaceutically acceptable bases such as those well known in the art. Suitable salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxyethyl)morpholine, 1-(2-hydroxyethyl) pyrrolidine, N-methyl glucamine, piperazine, triethanolamine or tromethamine. These salts may be prepared from compounds of formula I by known salt-forming procedures.

Compounds of formula I that contain acidic, e.g. carboxyl groups may also exist as zwitterions with the quaternary ammonium centre.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Many compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2$H and $^3$H, carbon e.g. $^{11}$C, $^{13}$C and $^{14}$C, chlorine e.g. $^{36}$Cl, fluorine e.g. $^{18}$F, iodine e.g. $^{123}$I and $^{125}$I, nitrogen e.g. $^{13}$N and $^{15}$N, oxygen e.g. $^{15}$O, $^{17}$O and $^{18}$O, and sulfur e.g. $^{35}$S.

Certain isotopically-labelled compounds of formula I, for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium ($^2$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. D$_2$O, d$_6$-acetone or d$_6$-DMSO.

Specific especially preferred compounds of the invention are those described hereinafter in the Examples.

The invention also provides a process for the preparation of compounds of formula I which comprises:

(i) (A) reacting a compound of formula II

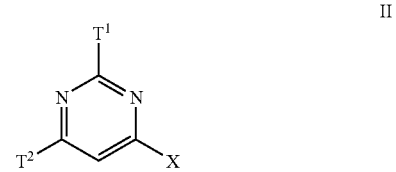

II where T$^1$ and T$^2$ are as hereinbefore defined and X is halo, with a compound of formula III T$^3$-L (III), wherein T$^3$ is as hereinbefore defined and L is a leaving group or under certain reaction conditions (e.g. where T$^3$ is a nucleophile) L may be absent; or (B) reacting a compound of formula IV

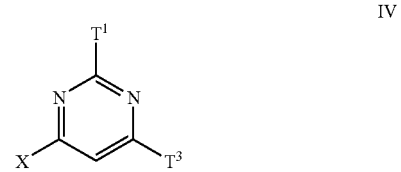

IV where T$^1$, and T$^3$ are as hereinbefore defined and X is halo, with a compound of formula V

V where T$^2$ is as hereinbefore defined; and (ii) recovering the product in free or salt or solvate form.

Process variant (A) may be effected using known procedures for reacting halogenated heterocyclic groups with nucleophiles or analogously as hereinafter described in the Examples. The reaction is conveniently carried out in an organic solvent, for example DMF, optionally in the presence of a base, for example potassium tert-butoxide. Suitable reaction temperatures are room temperature.

Process variant (B) may be effected using known procedures for reacting halogenated heterocyclic groups with heterocyclic boronic acids in the presence of a suitable catalyst such as tetrakis(triphenylphosphine)palladium or analogously as hereinafter described in the Examples. The reaction is conveniently carried out in an organic solvent, for example acetonitrile, tetrahydrofuran (THF) or dimethylethylene glycol (DME), optionally in the presence of an inorganic base, for example sodium carbonate. Suitable reaction temperatures are elevated temperatures, e.g. from 60° C. to 150° C., preferably by microwaving at about 90° C.

Compounds of formula II are formed by reacting a compound of formula VI

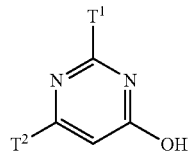
VI where $T^1$ and $T^2$ are as hereinbefore defined with a halogenating agent. This may be effected using known procedures for halogenating hydroxy compounds or analogously as hereinafter described in the Examples. The halogenating agent is preferably a combination of a strong Lewis acid e.g. $POCl_3$ and $PCl_5$. Suitable reaction temperatures are elevated temperatures, for example reflux temperature.

Compounds of formula III are known or may be prepared by known procedures.

Compounds of formula IV are formed by reacting a compound of formula VII

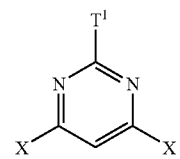
VII where $T^1$ is as hereinbefore defined and X is halo, with a compound of formula III This may be effected using known procedures for reacting halogenated heterocyclic groups with nucleophiles or analogously as hereinafter described in the Examples. The reaction is conveniently carried out in an organic solvent, for example isopropanol, in the presence of a suitable base, for example N,N-diisopropylethylamine (DIPEA). Suitable reaction temperatures are elevated temperatures, e.g. from 100° C. to 150° C., preferably by microwaving at about 130° C.

Compounds of formula V are known or may be prepared by known procedures.

Compounds of formula VI are formed by reacting a compound of formula VIII

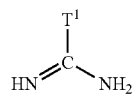
VIII where $T^1$ is as hereinbefore defined with a compound of formula IX

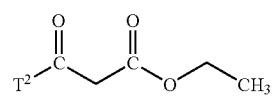
IX where $T^2$ is as hereinbefore defined. This may be effected using known procedures for reacting amidine with a β-ketoester or analogously as hereinafter described in the Examples. The reaction is conveniently carried out in an organic solvent, for example ethanol, preferably in the presence of an inorganic base sodium hydroxide. Suitable reaction temperatures are from 0° C. to 50° C., conveniently room temperature.

Compounds of formula VII are formed by reacting a compound of formula X

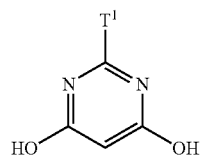
X where $T^1$ is as hereinbefore defined using known procedures for halogenating hydroxy compounds or analogously as hereinafter described in the Examples. The halogenating agent is preferably a combination of a strong Lewis acid e.g. $POCl_3$ and $PCl_5$. Suitable reaction temperatures are elevated temperatures, for example reflux temperature.

Compounds of formula VIII or IX are known or may be prepared by known procedures.

Compounds of formula X are formed by reacting a compound of formula VIII

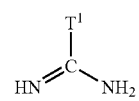
VIII where $T^1$ is as hereinbefore defined with a compound of formula XI

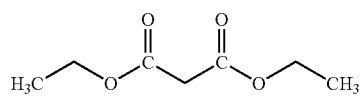
XI

This may be effected using known procedures for reacting amidine with a β-ketoester or analogously as hereinafter described in the Examples. The reaction is conveniently carried out in an organic solvent, for example methanol, preferably in the presence of an inorganic base, for example sodium methoxide, and preferably in an inert atmosphere (e.g. under argon). Suitable reaction temperatures are from 10° C. to 70° C., but preferably at about 55° C.

The compound of formula XI is known and may be prepared by known procedures.

Compounds of formula I or their pharmaceutically acceptable salts, hereinafter referred to alternatively as "agents of the invention", are useful as pharmaceuticals. Accordingly the invention also provides a compound of formula I or a pharmaceutically acceptable salt thereof for use as a pharmaceutical. The agents of the invention act as activin-like kinase ("ALK")-5 inhibitors. At least some agents of the invention also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins Smad2 and Smad3 at two carboxy terminal serines. The phosphorylated Smad proteins translocate into the nucleus and activate genes that contribute to the production of extracellular matrix. Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.*, 1994; 331(19), 1286-92. Further, TGF-β1 plays a role in the formation of fibronectin and plasminogen activator inhibitor-1, components of sclerotic deposits, through the action of Smad3 phosphorylation by the TGF-β1 receptor ALK5. Zhang Y., et al, *Nature*, 1998; 394(6696), 909-13; Usui T., et al, *Invest. Ophthalmol. Vis. Sci.*, 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.*, 1994; 331(19), 1286-92. TGF-β1 is elevated in acute and chronic glomerulonephritis Yoshioka K., et al, *Lab. Invest.*, 1993; 68(2), 154-63, diabetic nephropathy Yamamoto, T., et al, 1993, *PNAS* 90, 1814-1818, allograft rejection, HIV nephropathy and angiotensin-induced nephropathy Border W. A., et al, *N. Engl. 5 J. Med.*, 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing antibodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.*, 1996; 74(6), 991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol Physiol*, 1996; 23(3), 193-200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol (P<0.001) Blann A. D., et al, *Atherosclerosis*, 1996; 120(1-2), 221-6. Furthermore, SMC derived from human atherosclerotic lesions have an increased ALK5/TGF-β type II receptor ratio. Because TGF-β1 is overexpressed in fibroproliferative vascular lesions, receptor-I variant cells would be allowed to grow in a slow, but uncontrolled fashion, while overproducing extracellular matrix components McCaffrey T. A., et al, *Jr., J. Clin.; Invest.*, 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury. TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGF-βRII showed beneficial effects in a rat model of dimethylnitrosamine induced liver fibrosis (see Qi et al (1999) *Proc. Natl. Acad. Sci.* 96: 2345-9 and Nakamura et al (2000) *Hepatology* 32: 247-55). Inhibiting TGFβ expression using an antisense approach also reduced liver fibrosis induced by bile duct ligation (see Arias et al (2003) BMC *Gastroenterol* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol* 145: 166-77). Taken together these studies suggest that inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.*, 1995, 108, 985-1002. Moreover, TGF-β antibodies also improve healing of corneal wounds in rabbits Moller-Pedersen T., *Curr. Eye Res.*, 1998, 17, 736-747, and accelerate wound healing of gastric ulcers in the rat, Ernst H., *Gut*, 1996, 39, 172-175. These data strongly suggest that limiting the activity of TGF-β would be beneficial in many tissues and suggest that any disease with chronic elevation of TGF-β would benefit by inhibiting Smad2 and Smad3 signalling pathways.

TGF-β is also implicated in peritoneal adhesions Sand G. M., et al, *Wound Repair Regeneration*, 1999 November-December, 7(6), 504-510. Therefore, inhibitors of ALK5 would be beneficial in preventing peritoneal and sub-dermal fibrotic adhesions following surgical procedures.

TGF-β is also implicated in photoaging of the skin (see Fisher et al, Mechanisms of photoaging and chronological skin ageing, *Archives of Dermatology*, 138(11):1462-1470, 2002 November and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research*, 290(3):137-144, 1998 March).

TGF-β signalling is also implicated in the development of pulmonary disorders, in particular pulmonary hypertension and pulmonary fibrosis (see Morrell N W et al, Altered growth responses of pulmonary artery smooth muscle cells from patients with primary pulmonary hypertension to transforming growth factor-beta(1) and bone morphogenetic proteins *Circulation*. 2001 Aug. 14; 104(7): 790-5 and Bhatt N et al, Promising pharmacologic innovations in treating pulmonary fibrosis, *Curr Opin Pharmacol*. 2006 Apr. 28).

TGF-β1 levels are increased in animal models of pulmonary hypertension (Mata-Greenwood E et al, Alterations in TGF-beta1 expression in lambs with increased pulmonary blood flow and pulmonary hypertension, *Am. J. Physiol. Lung Cell Mol. Physiol* 2003 July; 285(1):L209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sakao S et al, Apoptosis of pulmonary microvascular endothelial cells stimulates vascular smooth muscle cell growth, *Am. J. Physiol. Lung Cell Mol. Physiol*. 2006 Apr. 14). Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N et al, Significance of elevated procollagen-III-peptide and transforming growth factor-beta levels of bronchoalveolar lavage fluids from idiopathic pulmonary fibrosis patients, *Tohoku J. Exp. Med*. 1997 February; 181(2): 285-95) and in animal models of idiopathic pulmonary fibrosis (Westergren-Thorsson G et al, Altered expression of small proteoglycans, collagen, and transforming growth factor-beta 1 in developing bleomycin-induced pulmonary fibrosis in rats, *J. Clin. Invest*. 1993 August; 92(2): 632-7).

Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge (Khalil N et al, Differential expression of transforming growth factor-beta type I and II receptors by pulmonary cells in bleomycin-induced lung injury: correlation with repair and fibrosis, *Exp. Lung. Res*. 2002 April-May; 28(3):233-50. Thus, inhibition of TGF-β1 activation of ALK5 is also indicated for pulmonary fibrosis.

TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signaling and overexpression of activin is linked to pathological disorders that involve extracellular matrix accumulation and fibrosis (e.g., Matsuse, T. et al., *Am. J. Respir Cell Mol. Biol*. 13:17-24 (1995); Inoue, S. et al., *Biochem. Biophys. Res. Comn*. 205:441-448 (1994); Matsuse, T. et al., *Am. J. Pathol*. 148:707-713 (1996); De Bleser et al., *Hepatology* 26:905-912 (1997); Pawlowski, J. E., et al., *J. Clin. Invest*. 100:639-648 (1997); Sugiyama, M. et al., *Gastroenterology* 114:550-558 (1998); Munz, B. et al., EMBO J. 18:5205-5215 (1999)), inflammatory responses (e.g., Rosendahl, A. et al., *Am. J. Respir. Cell Mol. Biol*. 25:60-68 (2001), cachexia or wasting (Matzuk7 M. M. et al., *Proc. Natl. Acad. Sci. USA* 91:8817-8821 (1994); Coerver, K. A. et al., *Mol. Endocrinol*. 10:531 543 (1996); Cipriano, S. C. et al., *Endocrinology* 141:2319-2327 (2000)), diseases or pathological responses in the central nervous system (e.g., Logan, A. et al., *Eur. J. Neurosci*. 11:2367-2374 (1999); Logan, A. et al., *Exp. Neurol*. 159:504-510 (1999); Masliah, E. et al., *Neurochem. Int*. 39:393-400 (2001); De Groot, C. J. A. et al., *J. Neuropathol. Exp. Neural*. 58:174-187 (1999); John, G. R. et al., *Nat. Med*. 8:1115-1121 (2002)) and hypertension (e.g., Dahly, A. J. et al., *Am. J. Physiol. Regul. Integr Comp. Physiol*. 283: R757-767 (2002)). Studies have shown that TGF-β and activin can act synergistically to induce extracellular matrix production (e.g., Sugiyama, M. et al., *Gastroerterology* 114; 550-558 (1998)).

It follows, therefore, that inhibition of ALK5 and/or ALK4 phosphorylation of Smad2 and Smad3 by the compounds of the present invention can be useful to treat and prevent disorders that involve these signaling pathways.

Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodeling associated with interstitial pulmonary fibrosis and pulmonary hypertension (Matsuse T et al, Expression of immunoreactive activin A protein in remodeling lesions associated with interstitial pulmonary fibrosis, *Am. J. Pathol*. 1996 March; 148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodeling observed in pulmonary fibrosis and hypertension (Ohga E et al, Effects of activin A on proliferation and differentiation of human lung fibroblasts, *Biochem. Biophys. Res. Commun.* 1996 Nov. 12; 228(2):391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F et al, Attenuation of bleomycin-induced pulmonary fibrosis by follistatin, *Am. J. Respir. Crit. Care Med.* 2005 Sep. 15; 172(6):713-20). Therefore, inhibiting activin signalling via ALK4 inhibition may also be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. *Proc. Natl. Acad. Sci. USA.* 2005 Dec. 27; 102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of a compound defined in the first aspect in the preparation of a medicament for treating or preventing a disease or condition mediated by ALK-5 inhibition or ALK-4 inhibition.

Diseases or condition mediated by ALK-5 inhibition or ALK-4 inhibition include glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neurological function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia.

Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific overexpression of myostatin in mice causes loss of muscle mass (Reisz-Porszasz et al (2003) *AJP—Endo.* 285:876-888), whereas myostatin null mice have increased skeletal muscle mass and reduced body fat (Lin et al (2002) *Biochem. Biophys. Res. Comm.* 291: 701-706). In accordance systemic administration of myostatin induces cachexia (Zimmers et al (2002) *Science* 296:1486-1488), whereas inhibition of myostatin by, for example, the myostatin neutralizing antibody JA16 increases muscle mass and strength in wildtype and dystrophic mdx mice (Bogdanovich et al (2002) *Nature* 420: 418-421.2002; Wagner et al (2002) *Ann. Neurol* 52: 832-836; Wolfman et al (2003) *Proc. Natl. Acad. Sci.* 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) *Am. J. Physiol Endocrinol. Metab.* 285: E363-371; Gonzales-Cadavid et al (1998) *Proc. Natl. Acad. Sci.* 95: 14938-14943; see also Reisz-Porszasz et al (2003) AJP—*Endo.* 285:876-888 and Jespersen et al (2006) *Scand. J. Med. Sci. Sports.* 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) *Ann. Rev. Dev. Biol.* 20: 61-86). Moreover, mature myostatin has been shown to act via activin type IIb and activin receptor like kinase (ALK) receptors in adipocytes (Rebbarpragada et al (2003) *Mol. Cell. Biol.* 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes a method for preventing or treating bone conditions which are associated with increased calcium depletion or resorption or in which stimulation of bone formation and calcium fixation in the bone is desirable in which an effective amount of a compound of formula I as defined above, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising a compound of formula I as defined above, or a pharmaceutically-acceptable and -cleavable ester, or acid addition salt thereof, in admixture with a pharmaceutically acceptable excipient, diluent or carrier.

The compounds of the Examples herein below generally have $IC_{50}$ values below 2 μM, and mostly below 1 μM. For instance, the compounds of Examples 1, 3, 6, 8 and 11 have $IC_{50}$ values of 0.335, 0.592, 0.261, 0.265 and 0.024 μM respectively.

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5

T204D is dissolved to 2.5 μg/ml in assay buffer (Assay buffer: 20 mM Tris-HCl pH 7.4, 10 mM MgCl$_2$, 2 mM MnCl$_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 μl of test or reference compound are added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 μl of dephosphorylated casein stock solution (dephosphorylated casein is dissolved in ddH$_2$O at 20 mg/ml) is added per well (200 μg/well final assay concentration). 20 μl of ALK5 T204D (2.5 μg/ml solution) is added per well (50 ng/well final assay concentration). The plates are left to incubate at room temperature for 10 minutes.

10 μl of ATP mix is added to the well to initiate the reaction (0.66 nM [$^{33}$P]ATP/1 μM unlabelled ATP/well final assay concentration). The ATP mix is prepared as follows, unlabelled ATP (3 mM) is dissolved in ddH$_2$O and pH adjusted to 7.4. The stock concentration of [$^{33}$P]ATP is 10 μCi/μl. The appropriate volume of [$^{33}$P]ATP is added to unlabelled ATP solution such that the final assay concentration per well is 0.1 μCi. Following addition of the ATP mix, the plates are incubated at room temperature for 50 minutes. The kinase reaction is terminated by the addition of 50 μL Stop Buffer (20 mM Tris-HCl pH 7.4, 10 mM EDTA).

75 μl/well from the reaction plate is transferred to a Multiscreen-IP plate (MultiScreen-IP plates are prepared by added 50 μL of 70% (v/v) ethanol per well and incubated for 5 minutes at room temperature. The ethanol is removed by aspiration via a MultiScreen HTS Vaccum Manifold unit (Millipore, Cat no: MSVMHT500). The plates are washed twice by adding 200 μl/well ddH$_2$O). The MultiScreen-IP plate is incubated at room temperature for 30 minutes to allowing binding of casein to the plate. The MultiScreen-IP plates are washed three times by adding 200 μl/well 100 mM phosphoric acid solution and the gasket is carefully removed from the back of the MultiScreen-IP plate and the plate dried in the oven for 30 minutes. The MultiScreen-IP plate is back-sealed, 50 μL of Microscint™20 is added, then the plates are topsealed and radiolabelled casein detected and quantified on a TopCount™ plate-reader using the $^{33}$P scintillation protocol.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone, fluticasone, ciclesonide or mometasone, or steroids described in WO 02/88167, WO 02/12266, WO 02/100879 or WO 02/00679 (especially those of Examples 3, 11, 14, 17, 19, 26, 34, 37, 39, 51, 60, 67, 72, 73, 90, 99 and 101), and non-steroidal steroid agonists such as those described in WO 00/00531, WO 02/10143, WO 03/82280, WO 03/82787, WO 03/104195 and WO 04/05229; LTB4 antagonists such as BIIL 284, CP-195543, DPC11870, LTB4 ethanolamide, LY 293111, LY 255283, CGS025019C, CP-195543, ONO-4057, SB 209247 and SC-53228, and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenyl-ethoxy)-propyl]-sulfonyl]ethyl]amino]ethyl]-2(3H)-benzothiazolone and pharmaceutically acceptable salts thereof (the hydrochloride being Viozan®-AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(TM) CC-10004 (Celgene), VM554/UM565 (Vernalis), T-440 (Tanabe), KW-4490 (Kyowa Hakko Kogyo) and GRC 3886 (Oglemilast, Glenmark), and those described in WO 92/19594, WO 93/19749, WO 93/19750, WO 93/19751, WO 98/18796, WO 99/16766, WO 01/13953, WO 03/39544, WO 03/104204, WO 03/104205, WO 04/00814, WO 04/00839 and WO 04/05258 (Merck), WO 04/18450, WO 04/18451, WO 04/18457, WO 04/18465, WO 04/18431, WO 04/18449, WO 04/18450, WO 04/18451, WO 04/18457, WO 04/18465, WO 04/019944, WO 04/19945, WO 04/45607, WO 04/37805, WO 04/63197, WO 04/103998, WO 04/111044, WO 05/12252, WO 05/12253, WO 05/13995, WO 05/30212, WO 05/30725, WO 05/87744, WO 05/87745, WO 05/87749 and WO 05/90345; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/86408, WO 04/39762, WO 04/39766, WO 04/45618 and WO 04/46083; and A2b antagonists such as those described in WO 02/42298 and WO 03/42214.

Such bronchodilatory drugs include beta-2 adrenoceptor agonists. Suitable beta-2 adrenoceptor agonists include albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

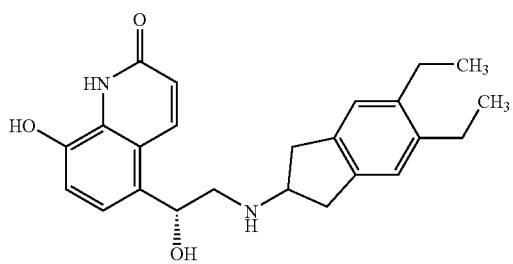 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular formoterol, carmoterol, ipratropium bromide, oxitropium bromide, tiotropium salts, glycopyrrolate, CHF 4226 (Chiesi) and SVT-40776, and also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistaminic/anti-allergic drug substances include acetaminophen, activastine, astemizole, azelastin, bamipin, cetirizine hydrochloride, cexchlorpheniramine, chlorophenoxamine, clemastine fumarate, desloratidine, dimenhydrinate, dimetinden, diphenhydramine, doxylamine, ebastine, emedastin, epinastine, fexofenadine hydrochloride, ketotifen, levocabastin, loratidine, meclizine, mizolastine, pheniramine, promethazine and tefenadine, as well as those disclosed in JP 2004107299, WO 03/099807 and WO 04/026841 (including any pharmacologically acceptable acid addition salts thereof which may exist).

According to a further embodiment of the invention, the agents of the invention may be employed as adjunct or adjuvant to other therapy, e.g. a therapy using a bone resorption inhibitor, for example as in osteoporosis therapy, in particular a therapy employing calcium, a ealeitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) $NH_2$ or PTS 893.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Especially preferred compounds of the present invention include compounds shown in Table 1 below, the method of preparation being described hereinafter.

TABLE 1

| Ex. | Structure | [M + H]$^+$ |
|---|---|---|
| 1 | 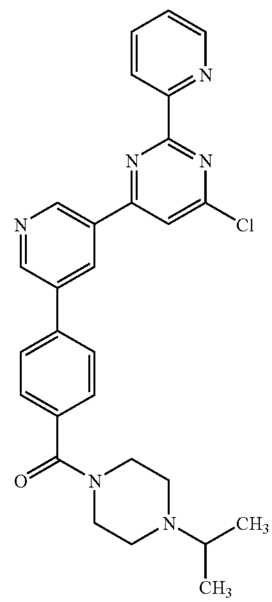 [SMILES: CC(C)N1CCN(C(=O)c2ccc(-c3cncc(-c4cc(Cl)nc(-c5ccccn5)n4)c3)cc2)CC1] | 499/501 |
| 2 | 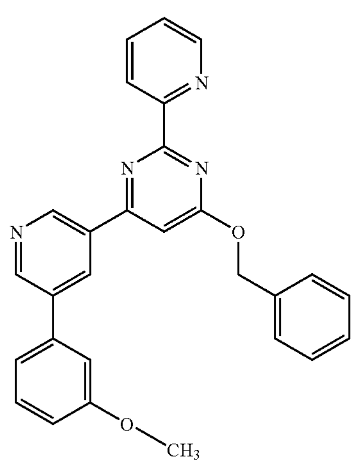 | 447 |

TABLE 1-continued

| Ex. | Structure | [M + H]$^+$ |
|---|---|---|
| 3 | 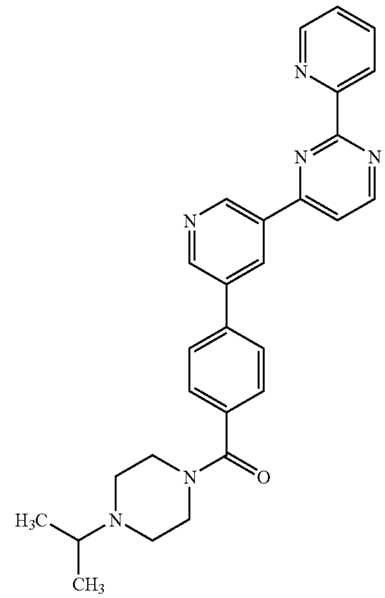 [SMILES: CC(C)N1CCN(C(=O)c2ccc(-c3cncc(-c4ccnc(-c5ccccn5)n4)c3)cc2)CC1] | 465 |
| 4 | 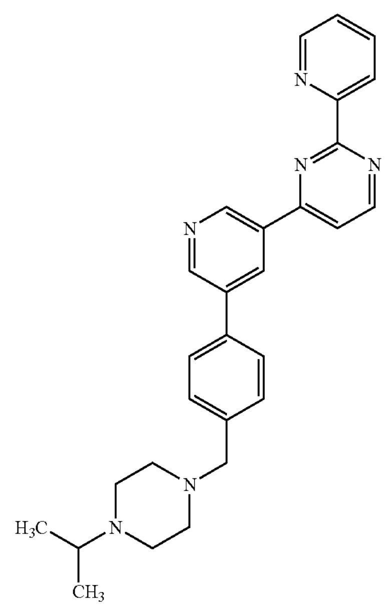 [SMILES: CC(C)N1CCN(Cc2ccc(-c3cncc(-c4ccnc(-c5ccccn5)n4)c3)cc2)CC1] | 451 |

TABLE 1-continued

| Ex. | Structure | [M + H]+ |
|---|---|---|
| 5 | 2-(pyridin-2-yl)-6-(pyridin-3-yl)-4-(2-(1H-indol-3-yl)ethoxy)pyrimidine | 394 |
| 6 | 2-(6-methylpyridin-2-yl)-6-(pyridin-3-yl)-4-(2-(1H-indol-3-yl)ethoxy)pyrimidine | 408 |
| 7 | 4-chloro-2-(6-methylpyridin-2-yl)-6-(5-(4-(4-isopropylpiperazine-1-carbonyl)phenyl)pyridin-3-yl)pyrimidine | 513/515 |
| 8 | 4-benzyloxy-2-(6-methylpyridin-2-yl)-6-(5-(4-(4-isopropylpiperazine-1-carbonyl)phenyl)pyridin-3-yl)pyrimidine | 585 |
| 9 | 4-methoxy-2-(6-methylpyridin-2-yl)-6-(5-(4-(4-isopropylpiperazine-1-carbonyl)phenyl)pyridin-3-yl)pyrimidine | 509 |

TABLE 1-continued

| Ex. | Structure | [M + H]+ |
|---|---|---|
| 10 | 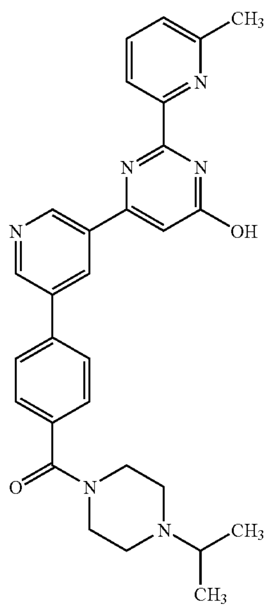 [SMILES: Cc1cccc(-c2nc(O)cc(-c3cncc(-c4ccc(C(=O)N5CCN(C(C)C)CC5)cc4)c3)n2)n1] | 495 |
| 11 | 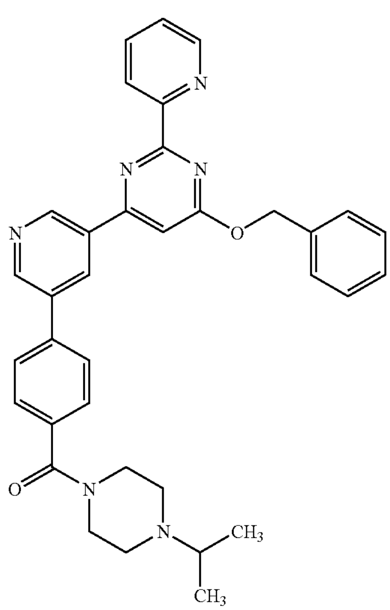 [SMILES: CC(C)N1CCN(C(=O)c2ccc(-c3cncc(-c4cc(OCc5ccccc5)nc(-c5ccccn5)n4)c3)cc2)CC1] | 571 |
| 12 | | 523 |
| 13 | | 479 |

TABLE 1-continued

| Ex. | Structure | [M + H]+ |
|---|---|---|
| 14 | 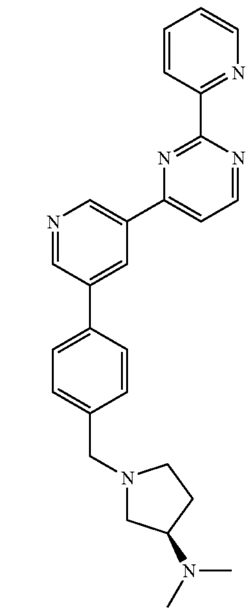 [SMILES: CN(C)[C@@H]1CCN(Cc2ccc(-c3cncc(-c4ccnc(-c5ccccn5)n4)c3)cc2)C1] | 437 |
| 15 | 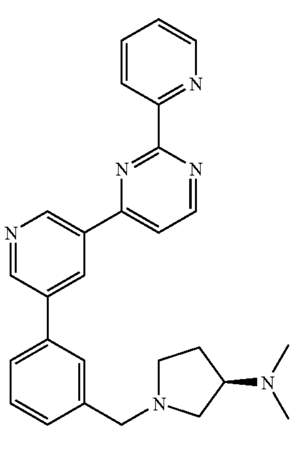 [SMILES: CN(C)[C@@H]1CCN(Cc2cccc(-c3cncc(-c4ccnc(-c5ccccn5)n4)c3)c2)C1] | 437 |
| 16 | | 499 |
| 17 | | 467 |

TABLE 1-continued

| Ex. | Structure | [M + H]+ |
|---|---|---|
| 18 | 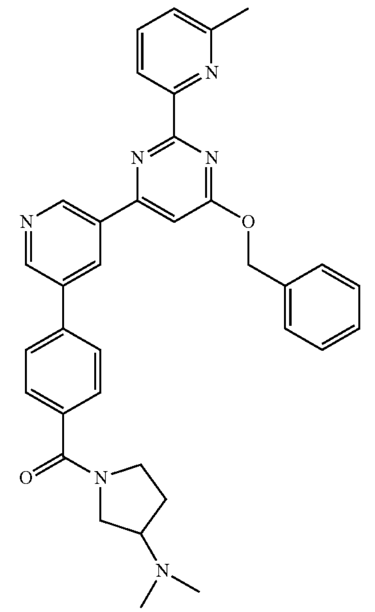 [SMILES: Cc1cccc(-c2nc(OCc3ccccc3)cc(-c3cncc(-c4ccc(C(=O)N5CCC(N(C)C)C5)cc4)c3)n2)n1] | 571 |
| 19 | 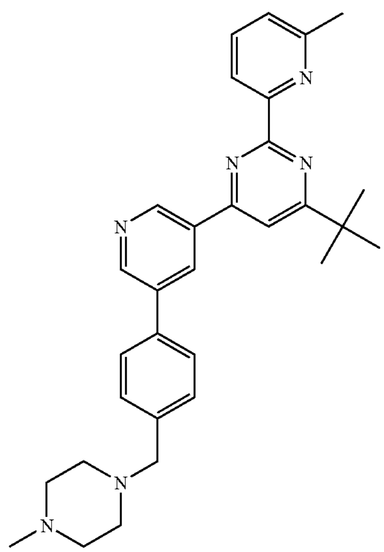 [SMILES: Cc1cccc(-c2nc(-c3cncc(-c4ccc(CN5CCN(C)CC5)cc4)c3)cc(C(C)(C)C)n2)n1] | 493 |

General Conditions:

Mass spectra are run on LCMS systems using electrospray ionization. These are either Agilent 1100 HPLC/Micromass Platform Mass Spectrometer combinations or Waters Acquity UPLC with SQD Mass Spectrometer. [M+H]+ refers to mono-isotopic molecular weights.

¹H-NMR: Run on either Bruker Ultrashield™ 400 (400 MHz) spectrometer or are run on Bruker AVANCE 400 NMR spectrometers using ICON-NMR. Spectra are measured at 298K and are referenced using the solvent peak, chemical shifts (δ-values) are reported in ppm, coupling constants (J) are given in Hz, spectra splitting pattern are designated as singlet (s), doublet (a), triplet (t), quadruplet (q), multiplet or more overlapping signals (m), broad signal (br), solvent is given in parentheses.

Abbreviations Used Have the Following Meanings:

AcOH is acetic acid, DCM is dichloromethane, DME is dimethylethylene glycol, DMF is dimethylformamide, TEA is triethylamine, Et₂O is diethyl ether, EtOAc is ethyl acetate, EtOH is ethanol, HATU is 2-(3H-[1,2,3]triazolo[4,5-b]pyridin-3-yl)-1,1,3,3-tetramethylisouronium hexafluorophosphate(V), h is hour, HPLC is high performance chromatography, MeCN is acetonitrile, MgSO₄ is magnesium sulphate, NaBH(OAc)₃ is sodium triacetoxyborohydride, NaOMe is sodium methoxide, NMP is N-methyl-2-pyrrolidinone, PdCl₂(dppf).DCM is [1,1-Bis(diphenylphosphino)-ferrocene]dichloropalladium(II) complex with dichloromethane, PdCl₂(PPh₃)₂ is dichlorobis(triphenylphosphine)-palladium(II), PS is polymer supported, RT is room temperature, SCX-2 is strong cation exchange (e.g. Isolute® SCX-2 columns from Biotage), TFA is trifluoroacetic acid and THF is tetrahydrofuran.

Preparation of Final Compounds

Example 1

{4-[5-(6-Chloro-2-pyridin-2-yl-pyrimidin-4-yl)-pyridin-3-yl]-phenyl}-(4-isopropyl-piperazin-1-yl)-methanone A solution of (4-Isopropylpiperazin-1-yl)(4-(5-(4,4,5,5-tetramethyl-[1,3,2]-dioxaborolan-2-yl)pyridin-3-yl)-phenyl)-methanone (Int. I) (1.5 eq, 402 mg) in DME (1 ml) and 2M sodium carbonate (0.62 ml) is treated with 4,6-dichloro-2-pyridin-2-yl-pyrimidine (Int. C) (1 eq, 139 mg) and placed under an atmosphere of argon. PdCl₂(dppf).DCM (0.1 eq. 45 mg) is added and the reaction mixture is heated using microwave radiation at 90° C. for 90 minutes. After cooling to room temperature, the mixture is partitioned between DCM/water and the organic portion is separated, washed with brine, dried (MgSO₄) and concentrated in vacuo. The crude residue is purified by chromatography on silica eluting with 0-10% MeOH in DCM to afford the title compound [M+H]+=499/501 as a solid.

Example 2

4-Benzyloxy-6-[5-(3-methoxy-phenyl)-pyridin-3-yl]-2-pyridin-2-yl-pyrimidine

Step 1: 4-Chloro-6-[5-(3-methoxy-phenyl)-pyridin-3-yl]-2-pyridin-2-yl-pyrimidine A solution of 5-(3-methoxy-phenyl)-pyridine boronic acid hydrochloride (Int. D) (1 eq, 59 mg) in DME (1 ml) and 2M sodium carbonate (0.4 ml) is treated with 4,6-dichloro-2-pyridin-2-yl-pyrimidine (Int. C) (1 eq, 50 mg) and placed under an atmosphere of argon. PdCl₂(dppf).DCM (0.1 eq. 16 mg) is added and the reaction mixture is heated using microwave radiation at 90° C. for 1 h. After cooling to room temperature, the mixture is partitioned between EtOAc/water and the organic portion is separated, washed with brine, dried (MgSO₄) and concentrated in vacuo. The crude residue is purified by reverse phase column chromatography (Isolute™ C18, 0-100% acetonitrile in water—0.1% TFA) and the appropriate fractions are combined and concentrated in vacuo. The residue is loaded onto a SCX-2 cartridge eluting with MeOH followed by 2M NH₃ in MeOH. The methanolic ammonia fractions are concentrated in vacuo and dried under vacuum overnight to afford the title compound [M+H]+=375/377.

Step 2: 4-Benzyloxy-6-[5-(3-methoxy-phenyl)-pyridin-3-yl]-2-pyridin-2-yl-pyrimidine To a suspension of potassium tert-butoxide (2 eq, 18.6 mg) in DMF (1 ml) is added benzyl alcohol (2 eq, 7.2 µl) under an inert atmosphere of argon. After stirring at RT for 15 minutes, the mixture is treated dropwise with a solution of 4-chloro-6-[5-(3-methoxy-phenyl)-pyridin-3-yl]-2-pyridin-2-yl-pyrimidine (1 eq, 31 mg) and then allowed to stir at RT for 5 hours. The reaction is quenched with water (4 ml) and the mixture is extracted with EtOAc. The organic extracts are combined, washed with brine, dried (MgSO$_4$) and concentrated in vacuo. The residue is loaded onto a SCX-2 cartridge (1 g) eluting with MeOH followed by 2M NH$_3$ in MeOH. The methanolic ammonia fractions are concentrated in vacuo and dried under vacuum overnight to afford the title compound [M+H]$^+$=447 as an oil.

Example 3

(4-Isopropyl-piperazin-1-yl)-{4-[5-(2-pyridin-2-yl-pyrimidin-4-yl)-pyridin-3-yl]-phenyl}-methanone A stirred solution of 4-(4-isopropylpiperazine-1-carbonyl)phenylboronic acid (Int. E) (1.2 eq, 53 mg) and 2M sodium carbonate solution (2 eq, 2 ml) in DME (1 ml) under an inert atmosphere of N$_2$ is treated with 4-(5-bromo-pyridin-3-yl)-2-pyridin-2-yl-pyrimidine (Int. H) (1 eq, 50 mg) followed by PdCl$_2$(dppf).DCM (0.1 eq, 13 mg). The mixture is heated using microwave radiation at 90° C. for 90 minutes and then allowed to cool to RT. The mixture is extracted with DCM and the organic extracts are washed with water. The solvent is removed in vacuo and the crude product is purified by reverse phase column chromatography (Isolute™ C18, 0-80% acetonitrile in water—0.1% TFA) and the appropriate fractions are combined and concentrated in vacuo. The residue is loaded onto a SCX-2 cartridge eluting with MeOH followed by 2M NH$_3$ in MeOH. The methanolic ammonia fractions are concentrated in vacuo and dried under vacuum overnight to afford the title compound [M+H]$^+$=465 as a yellow solid.

Example 4

4-{5-[4-(4-Isopropyl-piperazin-1-ylmethyl)-phenyl]-pyridin-3-yl}-2-pyridin-2-yl-pyrimidine This compound is prepared analogously to Example 3 by replacing 4-(4-isopropyl piperazine-1-carbonyl)phenylboronic acid (Int. E) with 4-((4-isopropylpiperazin-1-yl)methyl)phenylboronic acid (Int. F): [M+H]$^+$=451 as a yellow solid.

Example 5

3-[2-(6-Pyridin-3-yl-2-pyridin-2-yl-pyrimidin-4-yloxy)-ethyl]-1H-indole

Step 1: Mixture of 3-[2-(6-Pyridin-3-yl-2-pyridin-2-yl-pyrimidin-4-yloxy)-ethyl]-1H-indole and 2-[1-(6-Pyridin-3-yl-2-pyridin-2-yl-pyrimidin-4-yl)-1H-indol-3-yl]-ethanol The title mixture is prepared from 4-chloro-6-pyridin-3-yl-2-pyridin-2-yl-pyrimidine (Int. A) and 3-(2-hydroxyethyl)indole analogously to Example 2.

Step 2: 3-[2-(6-Pyridin-3-yl-2-pyridin-2-yl-pyrimidin-4-yloxy)-ethyl]-1H-indole

The mixture of Step 1 (1 eq, 111.7 mg) in DCM (8 ml) is treated with PS-tosyl chloride (8 eq, 1.44 g) followed by pyridine (16 ml). The mixture is shaken at RT for 48 hours and then filtered and washed with DCM (3×) and THF (3×). The filtrate is concentrated in vacuo and the resulting crude residue is purified by reverse phase column chromatography (C18, 0-100% acetonitrile in water—0.1% TFA) and the appropriate fractions are combined and concentrated in vacuo. The residue is loaded onto a SCX-2 cartridge eluting with MeOH followed by 2M NH$_3$ in MeOH. The methanolic ammonia fractions are combined and concentrated in vacuo and dried under vacuum overnight to afford the title compound [M+H]$^+$=394 as a gum.

Example 6

3-{2-[2-(6-Methyl-pyridin-2-yl)-6-pyridin-3-yl-pyrimidin-4-yloxy]-ethyl}-1H-indole This compound is prepared from 4-chloro-2-(3-methyl-pyridin-2-yl)-6-pyridin-3-yl-pyrimidine (Int. G) analogously to Example 5: [M+H]$^+$=408 as an oil.

Example 7

(4-{5-[6-Chloro-2-(6-methyl-pyridin-2-yl)-pyrimidin-4-yl]-pyridin-3-yl}-phenyl)-(4-isopropyl-piperazin-1-yl)-methanone This compound is prepared from 4,6-dichloro-2-(6-methyl-pyridin-2-yl)-pyrimidine (Int. B) and (4-isopropylpiperazin-1-yl)(4-(5-(4,4,5,5-tetramethyl-1,3,2-dioxaborolan-2-yl)pyridin-3-yl)phenyl)methanone (Int. I) analogously to Example 1: [M+H]$^+$=513/515 as a brown solid.

Example 8

(4-{5-[6-Benzyloxy-2-(6-methyl-pyridin-2-yl)-pyrimidin-4-yl]-pyridin-3-yl}-phenyl)-(4-isopropyl-piperazin-1-yl)-methanone This compound is prepared from (4-{5-[6-chloro-2-(6-methyl-pyridin-2-yl)-pyrimidin-4-yl]-pyridin-3-yl}-phenyl)-(4-isopropyl-piperazin-1-yl)-methanone (Ex. 7) analogously to Example 2: [M+H]$^+$=585 as a yellow solid.

Example 9

(4-Isopropyl-piperazin-1-yl)-(4-{5-[6-methoxy-2-(6-methyl-pyridin-2-yl)-pyrimidin-4-yl]-pyridin-3-yl}-phenyl)-methanone This compound is prepared from (4-{5-[6-chloro-2-(6-methyl-pyridin-2-yl)-pyrimidin-4-yl]-pyridin-3-yl}-phenyl)-(4-isopropyl-piperazin-1-yl)-methanone (Ex. 7) and methanol analogously to Example 2: [M+H]$^+$=509 as a white solid.

Example 10

(4-{5-[6-Hydroxy-2-(6-methyl-pyridin-2-yl)-pyrimidin-4-yl]-pyridin-3-yl}-phenyl)-(4-isopropyl-piperazin-1-yl)-methanone A solution of (4-{5-[6-benzyloxy-2-(6-methyl-pyridin-2-yl)-pyrimidin-4-yl]-pyridin-3-yl}-phenyl)-(4-isopropyl-piperazin-1-yl)-methanone (Example 8) (1 eq, 30 mg) in dry DCM (0.6 ml) under an atmosphere of N$_2$ is treated with trimethylsilyl iodide (12 eq, 83.6 µl). After stirring at RT overnight, the reaction is quenched by addition of MeOH (5 ml) and stirring continued for 45 minutes. The solvent is removed in vacuo and the residue is loaded onto a SCX-2 cartridge (1 g) eluting with MeOH followed by 2M NH$_3$ in MeOH. The methanolic ammonia fractions are combined and concentrated in vacuo and dried under vacuum overnight to afford the title compound [M+H]$^+$=495 as a white solid.

Example 11

{4-[5-(6-Benzyloxy-2-pyridin-2-yl-pyrimidin-4-yl)-pyridin-3-yl]-phenyl}-(4-isopropyl-piperazin-1-yl)-methanone This compound is prepared from {4-[5-(6-chloro-2-pyridin-2-yl-pyrimidin-4-yl)-pyridin-3-yl]-phenyl}-(4-isopropyl-piperazin-1-yl)-methanone (Ex. 1) analogously to Example 2: [M+H]$^+$=571 as a yellow solid.

$^1$H NMR (400 MHz, MeOD-d4) 9.39 (d, 2.04 Hz, 1H), 9.06 (m, 1H), 8.98 (d, 2.20 Hz, 1H), 8.78 (m, 1H), 8.64 (m, 1H), 8.05 (t, 1H), 7.97 (d, 8.36 Hz, 2H), 7.66-7.55 (m, 5H), 7.42-7.39 (m, 4H), 5.70 (s, 2H), 4.59 (br, 1H), 3.60 (br hump, 4H), 3.00 (br hump, 4H), 1.25 (d, 6.44 Hz, 6H).

Example 12

{4-[5-(6-Isopropoxy-2-pyridin-2-yl-pyrimidin-4-yl)-pyridin-3-yl]-phenyl}-(4-isopropyl-piperazin-1-yl)-methanone This compound is prepared from {4-[5-(6-chloro-2-pyridin-2-yl-pyrimidin-4-yl)-pyridin-3-yl]-phenyl}-(4-isopropyl-piperazin-1-yl)-methanone (Ex. 1) and isopropanol analogously to Example 2: [M+H]$^+$=523 as a pale yellow solid.

Example 13

4-tert-Butyl-6-{5-[4-(4-methyl-piperazin-1-ylmethyl)-phenyl]-pyridin-3-yl}-2-pyridin-2-yl-pyrimidine Step A: 3-Bromo-5-trimethylsilanylethynyl-pyridine To a solution of 3,5-dibromopyridine (1.0 eq, 5.0 g, 20.9 mmol) in TEA (100 ml) under an inert atmosphere of nitrogen is added copper(I) iodide (0.1 eq, 406 mg, 2.09 mmol) and PdCl$_2$(PPh$_3$)$_2$ (0.1 eq, 1.5 g, 2.09 mmol). Trimethylsilylacetylene (1.2 eq, 3.6 ml, 25 mmol) is added and the resulting mixture is stirred at room temperature for 2 h. The solvent is removed in vacuo and the residue is partitioned between water and DCM. The organic portion is separated and washed with sat. aqueous NaHCO$_3$ solution, dried (MgSO$_4$) and concentrated in vacuo. Purification by column chromatography (hexane/DCM) yields the title compound; [M+H]$^+$=254/256.

Step B: 1-(5-Bromo-pyridin-3-yl)-4,4-dimethyl-pent-1-yn-3-one

3-Bromo-5-trimethylsilanylethynyl-pyridine (1.0 eq, 1.22 g, 4.78 mmol), pivaloyl chloride (1.1. eq, 0.647 ml, 5.26 mmol) and copper(I) chloride (0.2 eq, 95 mg, 0.96 mmol) are dissolved in DMF (8 ml). The resulting mixture is heated using microwave radiation at 120° C. for 30 min. The mixture is filtered and washed with EtOAc. The filtrate is concentrated in vacuo and partitioned between sat. aqueous NaHCO$_3$ solution and EtOAc. The organic portion is separated, dried (MgSO$_4$) and concentrated in vacuo to afford the title compound; [M+H]$^+$=266/268.

Step C: 4-(5-Bromo-pyridin-3-yl)-6-tert-butyl-2-pyridin-2-yl-pyrimidine

To a solution of 1-(5-bromo-pyridin-3-yl)-4,4-dimethyl-pent-1-yn-3-one (1 eq, 770 mg, 2.89 mmol) in THF (12 ml) is added pyridine-2-carboxamidine (1.5 eq, 684 mg, 4.34 mmol) and Na$_2$CO$_3$ (2.4 eq, 736 mg, 6.94 mmol). The resulting mixture is heated using microwave radiation for 1 h at 150° C. The solvent is removed in vacuo and the residue is partitioned between sat. aqueous NaHCO$_3$ solution and DCM. The organic portion is dried (MgSO$_4$) and concentrated in vacuo. The resulting residue is purified using column chromatography (DCM/MeOH) to give the title compound; [M+H]$^+$=369/371.

Step D: 4-tert-Butyl-6-{5-[4-(4-methyl-piperazin-1-ylmethyl)-phenyl]-pyridin-3-yl}-2-pyridin-2-yl-pyrimidine To a solution of 4-(5-bromo-pyridin-3-yl)-6-tert-butyl-2-pyridin-2-yl-pyrimidine (1 eq, 200 mg, 0.542 mmol) in EtOH/DME (2 ml, 1:1) is added 4-(4-methyl-piperazin-1-ylmethyl)-phenyl-boronic acid (1.1 eq, 174 mg, 0.596 mmol), aqueous Na$_2$CO$_3$ solution (2 M, 3 eq, 0.812 ml, 1.63 mmol) and Pd(PPh$_3$)$_4$ (0.05 eq, 31 mg, 0.027 mmol). The resulting mixture is heated using microwave radiation for 20 min at 140° C. The mixture is filtered, washed with DCM and concentrated in vacuo. The residue is partitioned between sat. aqueous NaHCO$_3$ solution and DCM and the organic layer is washed with brine, dried (MgSO$_4$) concentrated under reduced pressure. The resulting residue is purified by reverse phase chromatography yielding the title compound; [M+H]$^+$=479. $^1$H NMR (CDCl$_3$, 400 MHz): 9.26 (d, 1H), 8.95 (d, 1H), 8.87 (m, 1H), 8.66 (t, 1H), 8.62 (m, 1H), 7.88 (td, 1H), 7.77 (s, 1H), 7.64 (d, 2H), 7.47 (d, 2H), 7.41 (ddd, 1H), 3.58 (s, 2H), 2.60-2.43 (m, 8H), 2.32 (s, 3H), 1.51 (s, 9H).

Example 14-15

These compounds namely,
Dimethyl-((R)-1-{4-[5-(2-pyridin-2-yl-pyrimidin-4-yl)-pyridin-3-yl]-benzyl}-pyrrolidin-3-yl)-amine (Ex. 14) and
Dimethyl-((R)-1-{3-[5-(2-pyridin-2-yl-pyrimidin-4-yl)-pyridin-3-yl]-benzyl}-pyrrolidin-3-yl)-amine (Ex. 15)
are prepared analogously to Example 4 using the appropriate boronic acid. These boronic acids can be prepared analogously to Intermediate F using the appropriate commercially available starting compounds.

Example 16

(4-{5-[6-Chloro-2-(6-methyl-pyridin-2-yl)-pyrimidin-4-yl]-pyridin-3-yl}-phenyl)-(3-dimethylamino-pyrrolidin-1-yl)-methanone This compound is prepared analogously to Example 7 by replacing 4-isopropylpiperazin-1-yl)(4-(5-(4,4,5,5-tetramethyl-1,3,2-dioxaborolan-2-yl)pyridin-3-yl)phenyl)methanone (Int. I) with the appropriate boronate ester. The boronate ester is prepared analogously to Intermediate I with the appropriate amine; [M+H]$^+$=499.

Example 17

(1-{4-[5-(6-Methoxy-2-pyridin-2-yl-pyrimidin-4-yl)-pyridin-3-yl]-benzyl}-pyrrolidin-3-yl)-dimethyl-amine This compound is prepared analogously to Example 9 by replacing 4-(4-isopropylpiperazine-1-carbonyl)phenylboronic acid (Int. E) with the appropriate boronic acid and by replacing 6-methyl-pyridine-2-carboxamidine with pyridine-2-carboxamidine. The boronic acid is prepared analogously to Intermediate F with the appropriate amine; [M+H]$^+$=467.

Example 18

(4-{5-[6-Benzyloxy-2-(6-methyl-pyridin-2-yl)-pyrimidin-4-yl]-pyridin-3-yl}-phenyl)-(3-dimethylamino-pyrrolidin-1-yl)-methanone This compound is prepared from (4-{5-[6-chloro-2-(6-methyl-pyridin-2-yl)-pyrimidin-4-yl]-pyridin-3-yl}-phenyl)-(3-dimethylamino-pyrrolidin-1-yl)-methanone (Ex. 16) and benzyl alcohol analogously to Example 8; [M+H]$^+$=571.

Example 19

4-tert-Butyl-6-{5-[4-(4-methyl-piperazin-1-ylmethyl)-phenyl]-pyridin-3-yl}-2-(6-methyl-pyridin-2-yl)-pyrimidine This compound is prepared analogously to Example 13 by replacing pyridine-2-carboxamidine (Step C) with 6-methyl-pyridine-2-carboxamidine (Int B. step 2); [M+H]$^+$=493

Preparation of Intermediate Compounds

Intermediate A

4-Chloro-6-pyridin-3-yl-2-pyridin-2-yl-pyrimidine

Step 1: 6-Pyridin-3-yl-2-pyridin-2-yl-3H-pyrimidin-4-one

Pyridine-2-carboxamide (1.2 eq, 3.76 g) in water (13 ml) is treated slowly with a solution of NaOH (1.5 eq, 1.6 g) in water (5 ml). Ethyl-3-pyridoyl acetate (1 eq, 3.76 g) in EtOH (5 ml) is then added slowly and the resulting mixture is stirred at room temperature overnight. The suspension which results is collected by filtration and washed with a minimal volume of water (approx. 5 ml). The solid is dried in a vacuum oven to afford the titled compound [M+H]$^+$=251.

Step 2: 4-Chloro-6-pyridin-3-yl-2-pyridin-2-yl-pyrimidine

To 6-pyridin-3-yl-2-pyridin-2-yl-3H-pyrimidin-4-one (1 eq, 0.26 mmol, 0.035 g) under inert atmosphere, is added dropwise phosphorus oxychloride (15 eq, 3.9 mmol, 0.36 ml) followed by cautious addition of phosphorus pentachloride (1 eq, 0.26 mmol, 0.054 g). After 4 hours at 100° C., the reaction mixture is added slowly to ice/water. The pH is adjusted to pH 7 using NaHCO$_3$ and the aqueous portion is extracted with EtOAc. The combined organic extracts are separated, washed with brine, dried (MgSO$_4$) and concentrated in vacuo. The crude product is purified by flash chromatography eluting with 0-100% MeOH in DCM to afford 4-chloro-6-pyridin-3-yl-2-pyridin-2-yl-pyrimidine as a white solid [M+H]$^+$=269/271.

Intermediate B 4,6-Dichloro-2-(6-methyl-pyridin-2-yl)-pyrimidine

Step 1: N-Methoxy-6-methyl-pyridine-2-carboxamidine

To a solution of 6-methyl-2-pyridinecarbonitrile (1 eq, 42.3 mmol, 5.00 g) in dry MeOH (20 ml) under an inert atmosphere of argon is added 0.5M sodium methoxide in MeOH (1.1 eq, 46.6 mmol, 93.1 ml) The reaction mixture is stirred at room temperature overnight and then concentrated in vacuo. The residue is dissolved in DCM and washed with water. The organic portion is dried (MgSO$_4$) and concentrated in vacuo to afford the title compound as an orange solid [M+H]$^+$=151.

Step 2: 6-Methyl-pyridine-2-carboxamidine

To a solution of N-methoxy-6-methyl-pyridine-2-carboxamidine (1 eq, 32.9 mmol, 4.94 g) in EtOH (40 ml) and water (10 ml) at room temperature is added ammonium chloride (1 eq, 32.9 mmol, 1.76 g). The resulting mixture is heated to 80° C. for 4 hours and then allowed to cool to room temperature overnight. The solvent is removed in vacuo to afford the title compound which is used in subsequent steps without further purification [2M+H]$^+$=271

Step 3: 2-(6-Methyl-pyridin-2-yl)-pyrimidine-4,6-diol

A solution of 6-methyl-pyridine-2-carboxamidine (step 2) (1.2 eq, 8.23 mmol, 1.41 g) in MeOH (5 ml) under an inert atmosphere of argon, at room temperature is treated with dimethyl malonate (1 eq, 6.86 mmol, 1.04 ml) and 0.5 M sodium methoxide in MeOH (3eq, 20.6 mmol, 41.2 ml). The resulting mixture is heated at reflux overnight and then allowed to cool to room temperature. The mixture is dry loaded onto silica and purification by flash chromatography eluting with 0-5% MeOH in DCM affords the title compound as a pale yellow solid [M+H]$^+$=204.

Step 4: 4,6-Dichloro-2-(6-methyl-pyridin-2-yl)-pyrimidine 2-(6-Methyl-pyridin-2-yl)-pyrimidine-4,6-diol (1 eq, 4.23 mmol, 859 mg) under an inert atmosphere of argon, is treated with phosphorus oxychloride (10 eq, 42.3 mmol, 3.87 ml) followed by phosphorus pentachloride (1 eq, 4.23 mmol, 879 mg) at room temperature. The resulting yellow suspension is heated at 105° C. for 6 hours and then allowed to cool to room temperature. Once cool, the mixture is added dropwise to ice water. The pH is adjusted to pH 7 using NaHCO$_3$ and the aqueous portion is extracted with EtOAc. The combined organic extracts are washed with brine, dried (MgSO$_4$) and concentrated in vacuo. The crude residue is dry loaded onto silica and purification by flash chromatography eluting with 100% DCM affords the title compound as a brown solid [M+H]$^+$=240/242.

Intermediate C 4,6-Dichloro-2-pyridin-2-yl-pyrimidine

This compound is prepared from pyridine-2-carboxamide analogously to Intermediate B.

Intermediate D 5-(3-Methoxy-phenyl)-pyridine boronic acid

Step 1: 3-Bromo-5-(3-methoxy-phenyl)-pyridine

A solution of 3-methoxy-phenylboronic acid (1.0 eq, 300 mg, 1.27 mmol) in DME (3 ml) and 2M sodium carbonate solution (1.2 ml) under an inert atmosphere of argon is treated with 3,5-dibromopyridine (300 mg, 1.27 mmol) followed by PdCl$_2$(dppf).DCM (0.1 eq, 93 mg) and then is heated using microwave radiation at 90° C. for 30 minutes. The mixture is extracted with DCM and the organic extracts are washed with water. The solvent is removed in vacuo and the crude product is purified by chromatography on silica eluting with 0-30% EtOAc in iso-hexane to afford the title compound [M+H]$^+$=265.

Step 2: 5-(3-Methoxy-phenyl)-pyridine boronic acid hydrochloride

A solution of 3-bromo-5-(3-methoxy-phenyl)-pyridine (180 mg, 0.68 mmol) in dry THF (3 ml) under an inert atmosphere of argon is treated with tri-isopropyl borate and then cooled to −78° C. The reaction mixture is treated dropwise with n-BuLi (2.5 M in hexanes) and then allowed to warm to room temperature over 2 hours. The reaction is quenched by slow addition of 2M HCl. The aqueous portion is washed with EtOAc and then concentrated in vacuo, until a solid precipitates. The solid is filtered and washed with water (1 ml) to afford the title compound [M+H]$^+$=230

Intermediate E 4-(4-Isopropylpiperazine-1-carbonyl)phenylboronic acid

A solution of 4-carboxyphenylboronic acid (1 eq, 213 mg) in DMF (5 ml) is treated with 1-isopropylpiperazine (1 eq, 155 mg) and the reaction mixture is stirred at RT for 10 minutes. TEA (1.2 eq, 0.202 ml) and HATU (2.4 eq, 1.104 g) are added and the resulting mixture is stirred at RT overnight. The reaction is quenched by addition of water and the mixture is extracted with DCM (2×). The combined organic portions are washed with brine, dried (MgSO$_4$) and concentrated in vacuo. The residue is dried in vacuo at 50° C. overnight to afford the title compound which is used without further purification [M+H]$^+$=277

Intermediate F 4-((4-Isopropylpiperazin-1-yl)methyl)phenylboronic acid

A cooled (0° C.) solution of 4-formaldehydephenyl boronic acid (1 eq, 1 g) in DCM (25 ml) is treated with isopropylpiperazine (1.2 eq, 1.03 g) followed by AcOH (1.2 eq, 0.48 ml) and NaBH(OAc)$_3$ (1.6 eq, 2.27 g). The reaction mixture is allowed to warm to room temperature and stirred for 4 hours. The mixture is then cooled (0° C.) and quenched with water (ca. 25 ml). The aqueous portion is washed with DCM (2×) and concentrated in vacuo to afford a yellow oil. The oil is dried in vacuo at 40° C. overnight and then triturated with DME (ca. 50 ml) to yield a solid which is filtered and dried to afford the title compound [M+H]$^+$=263.

Further boronic acids required to synthesise the Examples described herein can be prepared analogously to Intermediate D, E and F using the appropriate commercially available starting compounds.

Intermediate G

4-Chloro-2-(6-methyl-pyridin-2-yl)-6-pyridin-3-yl-pyrimidine

This compound is prepared analogously to Intermediate A by replacing pyridine-2-carboxamide (step 1) with 6-methyl-pyridine-2-carboxamidine (Int. B step 2).

Intermediate H 4-(5-Bromo-pyridin-3-yl)-2-pyridin-2-yl-pyrimidine

Step 1: (E)-1-(5-Bromo-pyridin-3-yl)-3-dimethyl-lamino-propenone

3-Acetyl-5-bromopyridine (1 eq, 0.2 g) and dimethoxymethyl-dimethyl-amine (2.5 eq, 133 μl) are heated at 100° C. for 1 hour. After cooling to RT, Et$_2$O/iso-hexane (10 ml of a 1:1 mixture) is added which results in the formation of a yellow precipitate. The solid is filtered and washed with Et$_2$O/iso-hexane (20 ml of a 1:1 mixture). The resulting solid is dried in vacuo at RT for 3 hours to afford the title compound as a beige solid [M+H]$^+$=255/257.

Step 2: 4-(5-Bromo-pyridin-3-yl)-2-pyridin-2-yl-pyrimidine

A solution of NaOMe (2.6 eq, 56 mg) in dry MeOH (3 ml) is stirred under N$_2$ at RT for 10 minutes and then treated with pyridine-2-carboxamidine (1 eq, 63 mg). After stirring at RT for 20 minutes, (E)-1-(5-bromo-pyridin-3-yl)-3-dimethyl-lamino-propenone (Step 1) (1 eq, 0.1 g) is added and the mixture is heated at reflux overnight. The reaction mixture is allowed to cool to RT and then the solvent is removed in vacuo. The residue is triturated with Et$_2$O (ca. 10 ml) and the resulting beige solid is filtered and washed with Et$_2$O to afford the title compound [M+H]$^+$=313/315.

Intermediate I (4-Isopropylpiperazin-1-yl)-(4-(5-(4,4,5,5-tetramethyl-[1,3,2]-dioxaborolan-2-yl)pyridin-3-yl)phenyl)-methanone Step 1: (4-Isopropylpiperazin-1-yl)-(4-(4,4,5,5-tetramethyl-[1,3,2]-dioxaborolan-2-yl)phenyl)-methanone 4-Carboxyphenyl boronate ester (1 eq, 0.5 g) in DMF (5 ml) is treated with HATU (2.4 eq, 1.82 g), TEA (1.2 eq, 334 μl) and N-isopropylpiperazine (1.2 eq, 343 μl) and stirred at RT for 90 minutes. The resulting mixture is partitioned between water and DCM and the organic portion is separated. The aqueous portion is extracted with DCM (3×) and the combined organic extracts are washed with brine, dried (MgSO$_4$) and concentrated in vacuo. The residue is dried in vacuo at 40° C. overnight to afford the title compound as a brown solid [M+H]$^+$=359.

Step 2: (4-(5-Bromopyridin-3-yl)phenyl)-(4-isopropylpiperazin-1-yl)-methanone

A solution of (4-isopropylpiperazin-1-yl)-(4-(4,4,5,5-tetramethyl-[1,3,2]-dioxaborolan-2-yl) phenyl)-methanone (step 1) (1.0 eq, 778 mg) in DME (4 ml) and 2M sodium carbonate solution (2 eq, 2.2 ml) is treated with 3,5-dibromopyridine (1 eq, 514 mg) followed by PdCl$_2$(dppf).DCM (0.1 eq, 159 mg). The resulting mixture is heated using microwave radiation at 90° C. for 1 h. The mixture is extracted with DCM and the organic extracts are washed with water. The solvent is removed in vacuo and the crude product is purified by chromatography on silica eluting with 0-100% EtOAc in iso-hexane followed by 0-5% MeOH in DCM to afford the title compound [M+H]$^+$=388/390.

Step 3: (4-Isopropylpiperazin-1-yl)-(4-(5-(4,4,5,5-tetramethyl-[1,3,2]-dioxaborolan-2-yl)pyridin-3-yl)phenyl)-methanone A suspension of (4-(5-bromopyridin-3-yl)phenyl)-(4-isopropylpiperazin-1-yl)-methanone (1 eq, 440 mg) (step 2) in DME (2 ml) under an atmosphere of $N_2$ is treated with dry potassium acetate (2 eq, 222 mg). A mixture of bis-(pinacolato)diboron (1.2 eq, 345 mg) and $PdCl_2$(dppf).DCM (0.04 eq, 33 mg) in DME (2 ml) are added to the suspension and the resulting mixture is heated using microwave radiation at 100° C. for 1 h. The mixture is filtered through Celite® (filter material) and concentrated in vacuo to afford the title compound which is used without further purification $[M+H]^+=354$.

The invention claimed is:

1. A compound in free or pharmaceutically acceptable salt form independently selected from:
   4-Benzyloxy-6-[5-(3-methoxy-phenyl)-pyridin-3-yl]-2-pyridin-2-yl-pyrimidine,
   (4-Isopropyl-piperazin-1-yl)-{4-[5-(2-pyridin-2-yl-pyrimidin-4-yl)-pyridin-3-yl]-phenyl}-methanone,
   4-{5-[4-(4-Isopropyl-piperazin-1-ylmethyl)-phenyl]-pyridin-3-yl}-2-pyridin-2-yl-pyrimidine,
   3-[2-(6-Pyridin-3-yl-2-pyridin-2-yl-pyrimidin-4-yloxy)-ethyl]-1H-indole,
   3-{2-[2-(6-Methyl-pyridin-2-yl)-6-pyridin-3-yl-pyrimidin-4-yloxy]-ethyl}-1H-indole,
   (4-{5-[6-Chloro-2-(6-methyl-pyridin-2-yl)-pyrimidin-4-yl]-pyridin-3-yl}-phenyl)-(4-isopropyl-piperazin-1-yl)-methanone,
   (4-{5-[6-Benzyloxy-2-(6-methyl-pyridin-2-yl)-pyrimidin-4-yl]-pyridin-3-yl}-phenyl)-(4-isopropyl-piperazin-1-yl)-methanone,
   (4-Isopropyl-piperazin-1-yl)-(4-{5-[6-methoxy-2-(6-methyl-pyridin-2-yl)-pyrimidin-4-yl]-pyridin-3-yl}-phenyl)-methanone,
   (4-{5-[6-Hydroxy-2-(6-methyl-pyridin-2-yl)-pyrimidin-4-yl-]pyridin-3-yl}-phenyl)-(4-isopropyl-piperazin-1-yl)-methanone,
   {4-[5-(6-Chloro-2-pyridin-2-yl-pyrimidin-4-yl)-pyridin-3-yl]-phenyl}-(4-isopropyl-piperazin-1-yl)-methanone,
   {4-[5-(6-Benzyloxy-2-pyridin-2-yl-pyrimidin-4-yl)-pyridin-3-yl]-phenyl}-(4-isopropyl-piperazin-1-yl)-methanone,
   {4-[5-(6-Isopropoxy-2-pyridin-2-yl-pyrimidin-4-yl)-pyridin-3-yl]-phenyl}-(4-isopropyl-piperazin-1-yl)-methanone,
   4-tert-Butyl-6-{5-[4-(4-methyl-piperazin-1-ylmethyl)-phenyl-]pyridin-3-yl}-2-pyridin-2-yl-pyrimidine,
   Dimethyl-((R)-1-{4-[5-(2-pyridin-2-yl-pyrimidin-4-yl)-pyridin-3-yl]-benzyl}-pyrrolidin-3-yl)-amine,
   Dimethyl-((R)-1-{3-[5-(2-pyridin-2-yl-pyrimidin-4-yl)-pyridin-3-yl]-benzyl}-pyrrolidin-3-yl)-amine,
   (4-{5-[6-Chloro-2-(6-methyl-pyridin-2-yl)-pyrimidin-4-yl-]pyridin-3-yl}-phenyl)-(3-dimethylamino-pyrrolidin-1-yl)-methanone,
   (1-{4-[5-(6-Methoxy-2-pyridin-2-yl-pyrimidin-4-yl)-pyridin-3-yl]-benzyl}-pyrrolidin-3-yl)-dimethyl-amine,
   (4-{5-[6-Benzyloxy-2-(6-methyl-pyridin-2-yl)-pyrimidin-4-yl-]pyridin-3-yl}-phenyl)-(3-dimethylamino-pyrrolidin-1-yl)-methanone,
   4-tert-Butyl-6-{5-[4-(4-methyl-piperazin-1-ylmethyl)-phenyl-]pyridin-3-yl}-2-(6-methyl-pyridin-2-yl)-pyrimidine,
   and free or salt or solvate forms thereof.

2. A compound according to claim 1 in combination with another drug substance which is an anti-inflammatory, a bronchodilator, an antihistamine, a decongestant or an anti-tussive drug substance.

3. A pharmaceutical composition comprising as active ingredient a compound according to claim 1 and a suitable pharmaceutically acceptable excipient.

* * * * *